United States Patent
Bryant et al.

(10) Patent No.: US 8,146,329 B2
(45) Date of Patent: Apr. 3, 2012

(54) METHOD OF PACKAGING A SURGICAL CABLE

(75) Inventors: Mark Alan Bryant, Auburn, IN (US); Elizabeth E. Nelson, Gwinn, MI (US); Tim K. Matulewicz, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 0 days.

(21) Appl. No.: 12/772,877

(22) Filed: May 3, 2010

(65) Prior Publication Data

US 2010/0326860 A1 Dec. 30, 2010

Related U.S. Application Data

(60) Provisional application No. 61/174,792, filed on May 1, 2009.

(51) Int. Cl.
*B65B 63/04* (2006.01)
(52) U.S. Cl. ............ 53/430; 53/118
(58) Field of Classification Search .......... 53/430, 53/118
See application file for complete search history.

(56) References Cited

U.S. PATENT DOCUMENTS

| | | | |
|---|---|---|---|
| 2,615,565 A * | 10/1952 | Bower et al. | 206/63.3 |
| 3,301,393 A * | 1/1967 | Regan, Jr. et al. | 206/409 |
| 3,495,703 A * | 2/1970 | Calabrese | 206/63.3 |
| 3,731,793 A * | 5/1973 | Hagel | 206/397 |
| 3,972,418 A | 8/1976 | Schuler et al. | |
| 4,084,692 A | 4/1978 | Bilweis | |
| 4,846,343 A | 7/1989 | Rupert | |
| 5,031,775 A | 7/1991 | Kane | |
| 5,156,267 A | 10/1992 | Yates, Jr. et al. | |
| 5,201,495 A | 4/1993 | Crates et al. | |
| 5,228,565 A | 7/1993 | Sinn | |
| 5,246,104 A | 9/1993 | Brown et al. | |
| 5,249,671 A * | 10/1993 | Sinn | 206/63.3 |
| 5,263,585 A | 11/1993 | Lawhon et al. | |
| 5,284,240 A | 2/1994 | Alpern et al. | |
| 5,407,071 A * | 4/1995 | Lawhon et al. | 206/388 |
| 5,415,658 A | 5/1995 | Kilpela et al. | |
| 5,456,722 A | 10/1995 | McLeod et al. | |
| 5,468,252 A * | 11/1995 | Kaplan et al. | 606/228 |
| 5,568,865 A | 10/1996 | Mase et al. | |
| 5,575,382 A * | 11/1996 | Sobel et al. | 206/63.3 |
| 5,649,927 A | 7/1997 | Kilpela et al. | |
| 5,667,155 A * | 9/1997 | Cerwin et al. | 242/472.5 |
| 5,669,501 A | 9/1997 | Hissong et al. | |
| 5,741,260 A | 4/1998 | Songer et al. | |
| 5,788,697 A | 8/1998 | Kilpela et al. | |
| 5,848,691 A | 12/1998 | Morris et al. | |
| 5,875,893 A | 3/1999 | Lee et al. | |
| 5,957,282 A | 9/1999 | Juszkiewicz et al. | |
| 6,068,121 A | 5/2000 | McGlinch | |
| 6,231,564 B1 | 5/2001 | Gambale | |

(Continued)

*Primary Examiner* — Hemant M Desai
(74) *Attorney, Agent, or Firm* — Fitch, Even, Tabin & Flannery, LLP

(57) ABSTRACT

A surgical cable packaging system and method are provided including, in one aspect, a cable holder having an upper portion and a lower portion. The upper and lower portions may have cooperating structures configured to be coupled together to form an interior space in which the cable is coiled. The cable holder may have an opening through which the cable extends to allow the cable to be removed from the interior space. In another aspect, a method of inserting a surgical cable into a cable holder comprising wrapping the cable around a body portion of a fixture and sliding the cable into an interior space of the cable holder in a coiled configuration.

6 Claims, 12 Drawing Sheets

U.S. PATENT DOCUMENTS

| | | | |
|---|---|---|---|
| 6,367,629 B1 * | 4/2002 | Bautista et al. | 206/388 |
| 6,387,099 B1 | 5/2002 | Lange et al. | |
| 6,605,091 B1 | 8/2003 | Iwanski | |
| 6,689,140 B2 | 2/2004 | Cohen | |
| 6,719,135 B2 | 4/2004 | Armijo | |
| 7,316,318 B1 | 1/2008 | Rosten et al. | |
| 7,452,360 B2 | 11/2008 | Trudeau et al. | |
| 7,621,880 B2 | 11/2009 | Ryan et al. | |
| 7,640,714 B2 | 1/2010 | Waller et al. | |
| 2010/0042106 A1 | 2/2010 | Bryant et al. | |

* cited by examiner

METHOD OF PACKAGING A SURGICAL CABLE

CROSS-REFERENCE TO RELATED APPLICATION

This application claims the benefit of U.S. Provisional Application No. 61/174,792, filed May 1, 2009, which is hereby incorporated by reference as if fully set forth herein.

FIELD

This application relates to packaging systems and, more particularly, to packaging systems for surgical cables and methods of packaging surgical cables.

BACKGROUND

Surgical cables are used in various surgical procedures to secure implants to bones or to hold fractured bones together. Surgical cables may be made from braided stainless steel, titanium, or synthetic polymer in monofilament or braided configurations. For example, one type of surgical cable is made from a plurality of braided stainless steel fibers with a connector at one end of the cable and a free end at the other. The connector includes an opening that receives the free end and a set screw for fixing the free end within the connector. In one instance, a surgeon joins fractured bones together by looping the cable around the bone fragments, feeding the free end of the cable through the opening in the connector, pulling the free end to constrict the loop of the cable about the bone fragments, and tightening the set screw to fix the constricted cable about the bone fragments.

Surgical cables may be individually packaged within sterile packaging and opened in an operating room. In one approach, a surgical cable is wound into a coil and inserted into a plastic pouch. The cable tends to expand within the pouch, which can cause twisting or kinking of the cable. Twisting or kinking of the cable may produce bends that could weaken the cable or inhibit a surgeon from feeding the cable through a cable tensioning device. Further, because a resilient cable may store potential energy when the cable is coiled, removing the cable from the pouch causes release of the energy and causes the cable to rapidly uncoil, which may make the cable difficult to handle.

In another approach, a surgical cable is packaged within a tray having a removable cover. The cable is loaded into the tray by pressing the cable into a channel formed in the tray. This process is labor intensive, as the cable may have to be pressed into the channel one section of the cable at a time. Further, because the cable resists being in the coiled configuration within the pouch, the cable is difficult to insert into the tray. Longer or more rigid cables compound the difficulties present in this approach.

A surgeon or operating room technician may peel the cover off of the tray and remove the surgical cable by pulling the cable outward from the channel. The cable may be coiled upon itself within the channel such that removing the cable from the tray entails pulling the coiled surgical cable outward from the tray. The resilient properties of the surgical cable may cause portions of the cable to rapidly uncoil, twist, or otherwise impair handling of the cable as the cable is withdrawn from its original orientation within the tray. Quickly withdrawing the cable from the tray may magnify the difficulty of handling the surgical cable.

BRIEF DESCRIPTION OF THE DRAWINGS

FIG. 5 is a perspective exploded view of the cable holder of FIG. 2 showing coupling structures of the upper and lower portions of the cable holder, and the orientation of the cable for being received in;

DETAILED DESCRIPTION OF THE PREFERRED EMBODIMENTS

Figure 1:
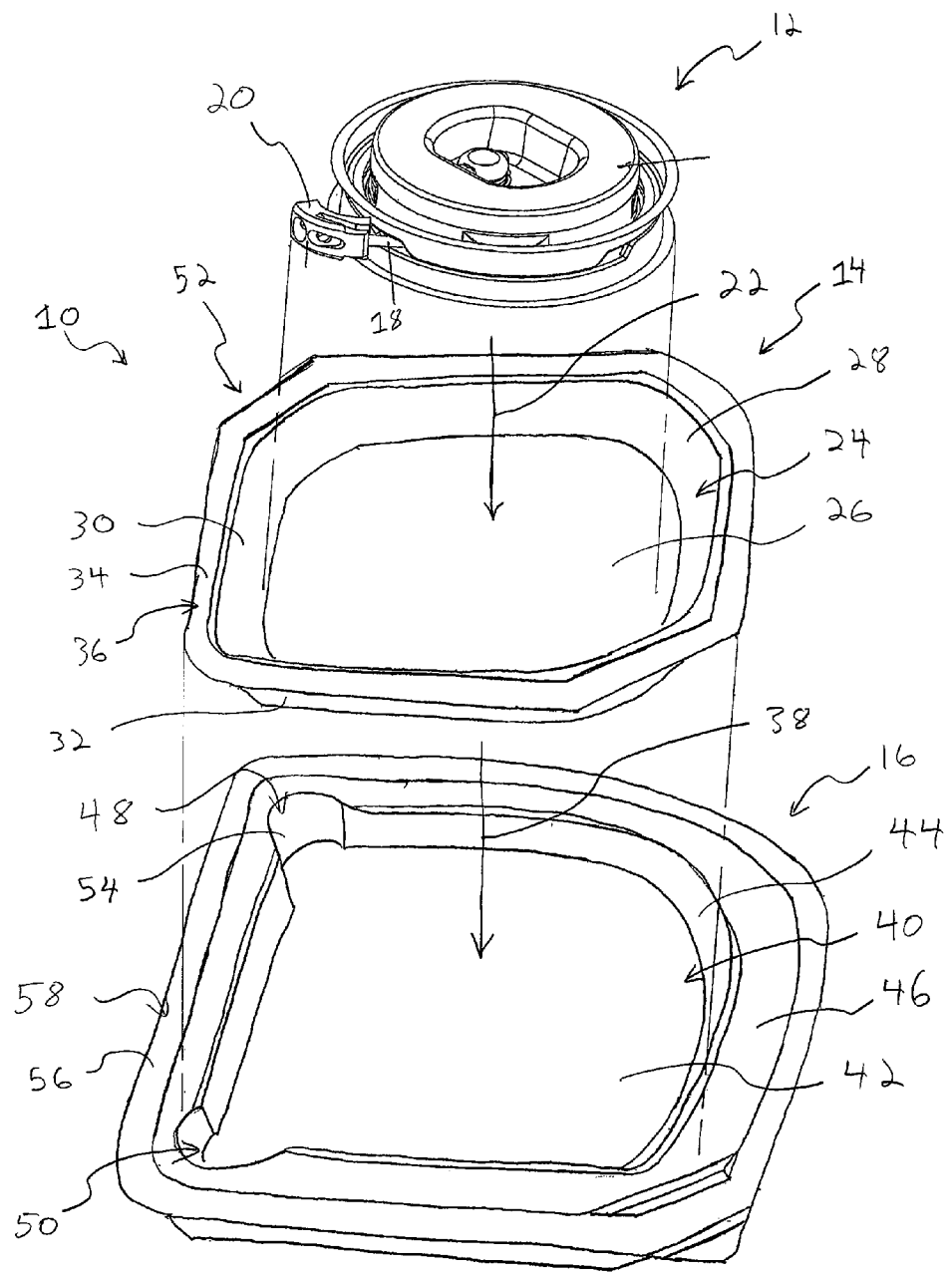
FIG. 1 is an exploded perspective view of a packaging system for storing a surgical cable showing a cable holder, an inner tray, and an outer tray.

In accordance with one aspect, an apparatus for receiving a surgical cable is provided that includes a cable holder having an annular configuration. The cable holder has upper and lower portions having outer cooperating structures configured for coupling the upper and lower portions together. The coupling of the upper and lower portions provides an interior space for holding a coiled surgical cable such that the cable holder may be quickly and easily assembled to contain the cable. Further, the cable holder may have an opening through which the cable extends to allow the cable to be removed from the interior space. In one approach, the cable extending through the opening may be grasped and pulled away from the cable holder to withdraw the cable from the interior space. Withdrawing the cable through the opening in the cable holder permits the cable to transition from a coiled configuration within the cable holder to an uncoiled or relaxed and elongated configuration outside of the cable holder while restricting the cable from rapidly uncoiling or twisting as the cable is withdrawn. In one form, the controlled release of the potential energy stored within the coiled cable permits the cable to be withdrawn using a single linear motion.

In accordance with another aspect, an apparatus for storing a surgical cable is provided that includes an annular side wall portion between upper and lower wall portions which extends farther radially than the upper and lower wall portions. The upper, side, and lower wall portions define an interior space with the upper, side, and lower wall portions cooperating to confine a surgical cable in the space. One or more of the wall portions may include an opening through which the cable extends for being pulled out from the interior space. The apparatus provides cost-efficient packaging for the surgical cable and permits the cable to be rapidly removed from the interior space defined by the wall portions.

A method of packaging a surgical cable is also provided. The method includes connecting a fixture to a lower portion of a cable holder and wrapping the cable in a helical manner around an elongate body portion of the fixture. Wrapping the cable about the fixture permits one to quickly and easily obtain a coiled configuration of the cable about the fixture. The coiled cable can then be displaced from the fixture into the cable holder. More particularly, the coiled cable can be displaced into the lower portion of the cable holder.

By one approach, displacing the cable from the fixture includes maintaining the coiled configuration of the cable such that the coiled surgical cable can be easily placed in the lower portion of the cable holder. The fixture can then be disconnected from the lower portion of the cable holder. Once the fixture has been disconnected from the lower portion, an upper portion of the cable holder may be coupled to the lower portion to form an interior space for retaining the cable therein. By this method, a coiled cable may be rapidly positioned within the cable holder.

In FIG. 1, a surgical cable package 10 including a cable holder 12, inner tray 14, and an optional outer tray 16 is shown. The cable holder 12 is configured to confine a cable 18 therein with a connector 20 at one end of cable positioned outside of the cable holder 12. The inner tray 14 and the outer tray 16 will be discussed in greater detail below in conjunction with FIGS. 8 and 9.

Figure 2:
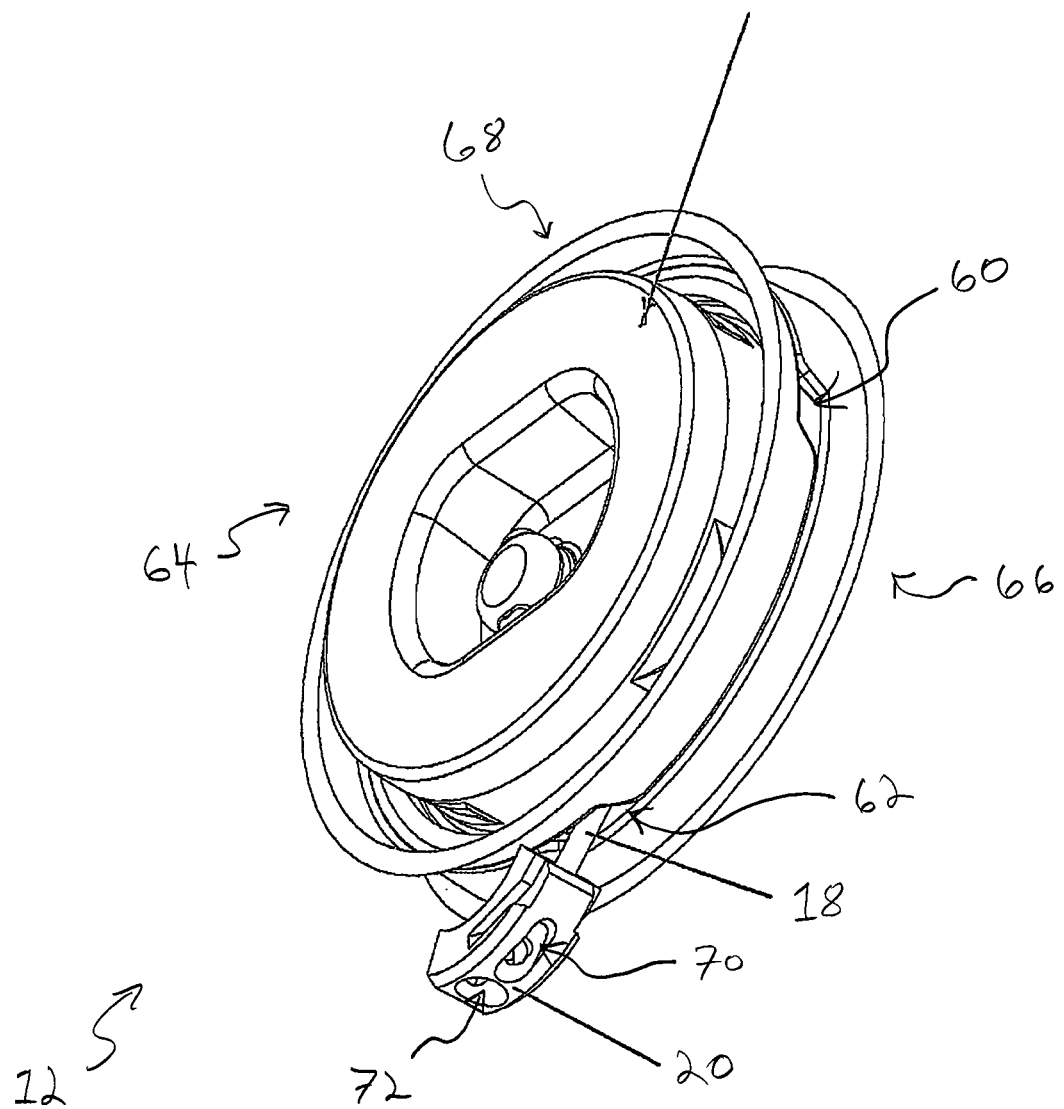
FIG. 2 is a perspective view of the cable holder of FIG. 1 showing the cable holder assembled to hold a cable therein a connector end of the cable extending outside of the cable holder.

Turning to FIG. 2, an isometric view of the cable holder 12 is shown to illustrate openings 60, 62 in the outer periphery of the cable holder 12 through which the surgical cable 18 may extend. As shown, one end of the surgical cable 18 extends through opening 62 which is spaced from opening 60 about the circumference of the cable holder 12. In one form, the cable holder 12 has four openings, but fewer or additional openings can be provided, if desired. Any one of the openings may be used to receive the surgical cable 18 during assembly of the cable holder 12. The cable holder 12 has an upper portion 64 and a lower portion 66, both of which may have a generally circular outer perimeter or edge. In one form, the upper portion 64 and lower portion 66 have the same circular shape with the same diameter. If desired, however, the upper and lower portions 64, 66 may have dissimilar shapes, different diameters, and may be elliptical, rectangular, or otherwise shaped.

The surgical cable may be attached to a connector 20 with an opening 70 configured to receive a free end of the cable 18. During surgery, the free end of the cable may be inserted through the opening 70 and fixed therein via installation of a set screw inserted in opening 72 of the connector 20 in communication with opening 70. In one aspect, the cable 18 and connector 20 may be similar to structures disclosed in U.S. Pat. No. 5,415,658, which issued on May 16, 1995 to Kipela et al., and which is hereby incorporated by reference as if fully set forth herein.

Figure 3:
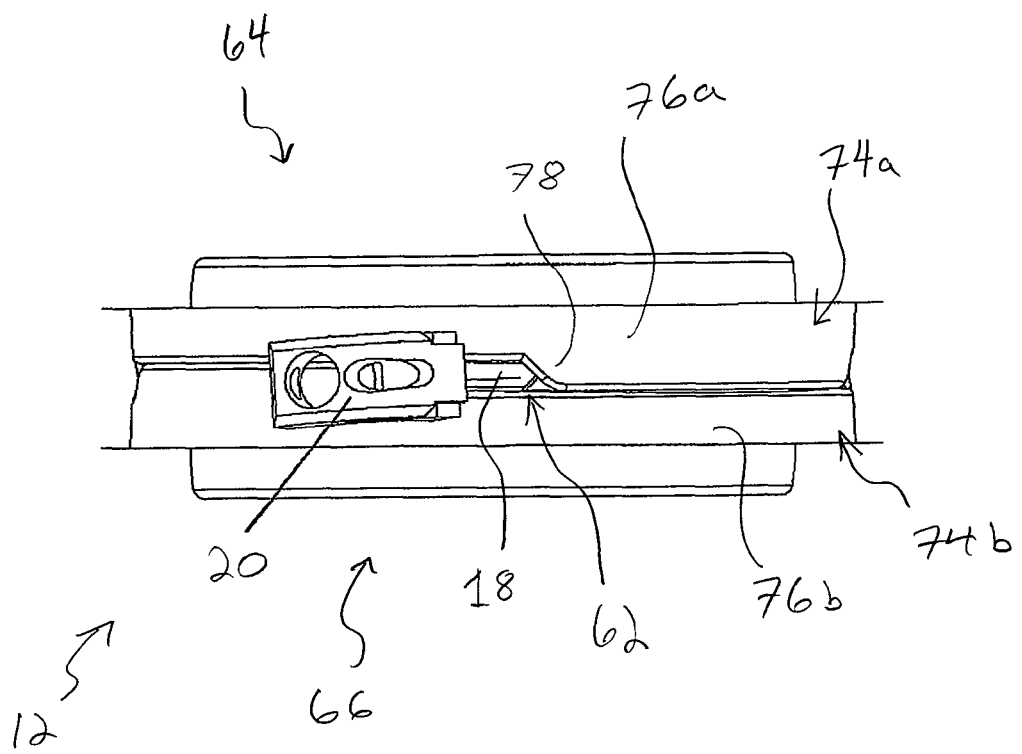
FIG. 3 is an elevational view of the cable holder of FIG. 2 showing outer walls of the cable holder that cooperate to form an opening through which the connector end of the cable extends.

In FIG. 3, the cable holder 12 is shown with cooperating structures 74a, 74b of the upper portion 64 and the lower portion 66, respectively, in the form of a circumferential wall portion 76a, 76b. The circumferential wall portions 76a, 76b include one or more guide structures 78 that define a portion of the opening 62 and guide the cable 18 outward from within the cable holder 12 (see reference numerals 153 and 155 in FIG. 7). As will be discussed below, the cooperating structures 74a, 74b also include walls disposed within the cable holder 12 (such as walls 110a, 118a shown in FIG. 4) that further define the opening 62 and function to guide the cable 18 outward from within the cable holder 12.

Figure 4:
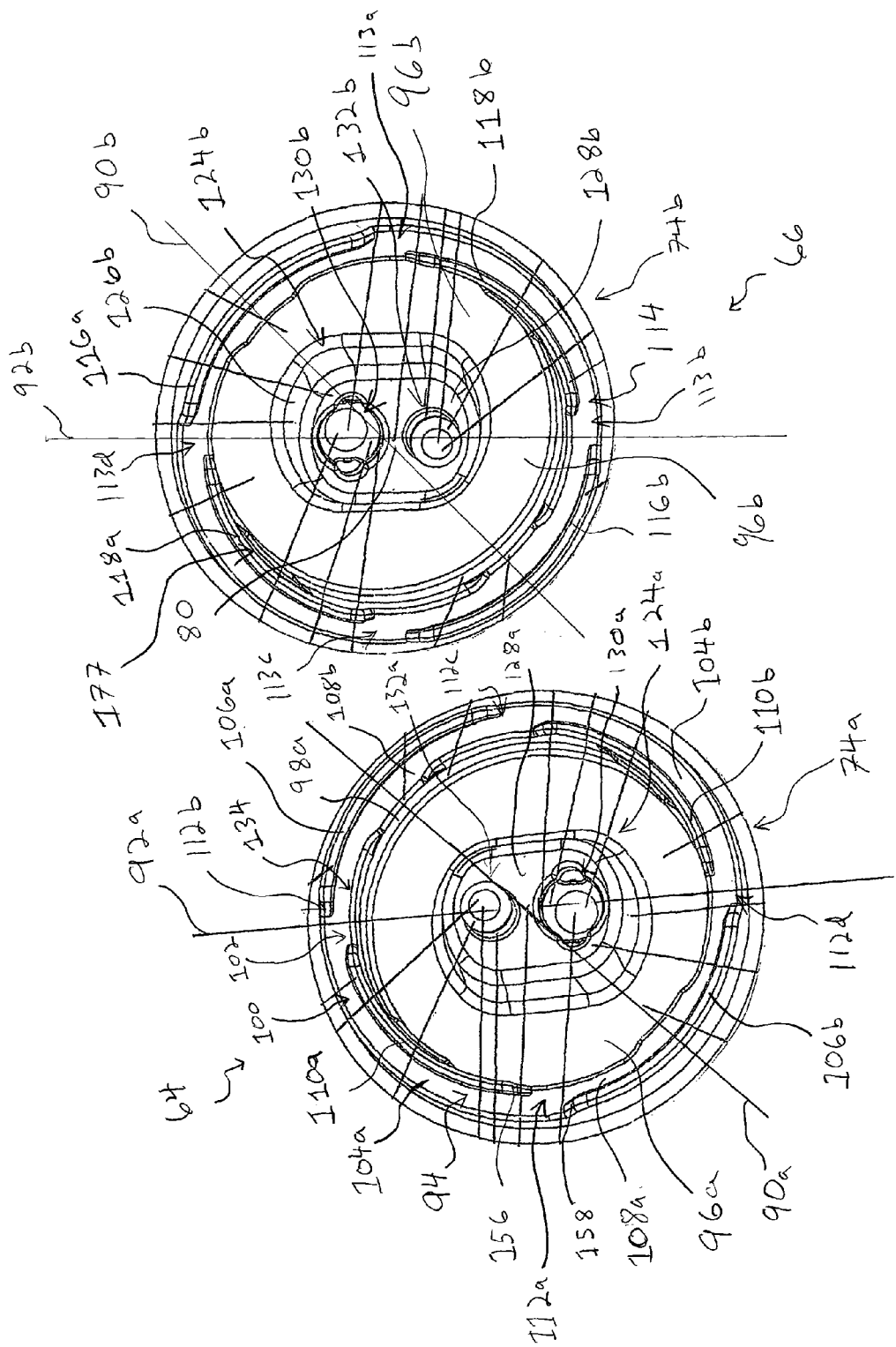
FIG. 4 is a perspective view of the cable holder of FIG. 2 showing an upper portion of the cable holder separated from a lower portion of the cable holder, the upper and lower portions having circumferentially extending walls that form a frictional lock when the upper and lower portions are connected.

With respect to FIG. 4, the upper portion 64 and the lower portion 66 of the cable holder 12 are illustrated separately to show the internal structures of each portion. In one form, the upper portion 64 and the lower portion 66 may be substantially identical to one another. FIG. 4 depicts two substantially identical upper and lower portions with the lower portion 66 rotated 180° about a centerpoint 80 from the orientation of the upper portion 64. In the illustrated embodiment, the around the cooperating structure 74a, 74b of the upper and lower portions 64, 66 are each symmetrical about a respective axis 90a, 90b. Further, the cooperating structure 74a, 74b of the upper and lower portions 64, 66 are asymmetrical about respective axes 92a, 92b around the circumferential walls 76a, 76b. In one approach, the configuration of the cooperating structures 74a, 74b restricts coupling of the upper and lower portions 64, 66 to a limited number of predetermined orientations.

Figure 5:
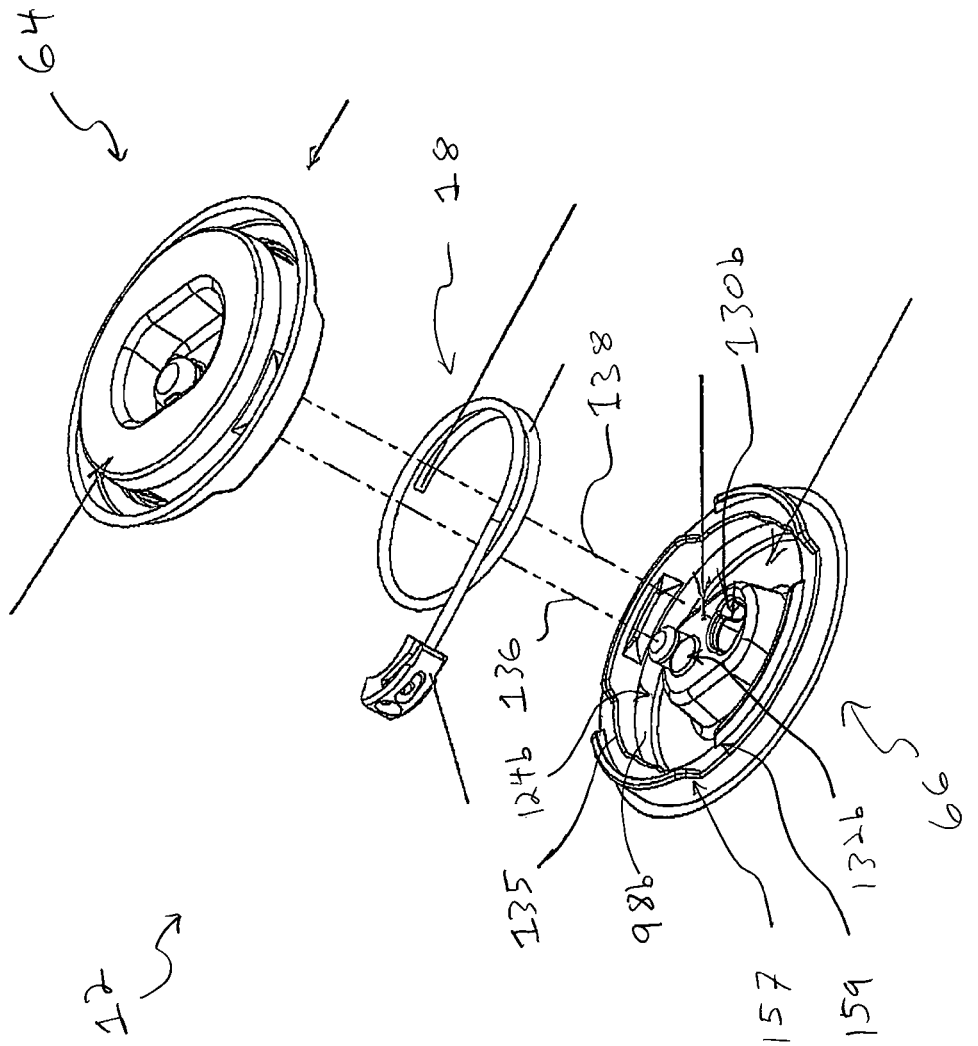

Turning to the details of the upper and lower portions 64, 66 (described herein in reference to upper portion 64), upper portion 64 has an outer annular wall 94, a lower wall 96a, and an upstanding side wall 98a extending between the annular wall 94 and the lower wall 96. A similar upstanding side wall 98b of the lower portion 66 is shown in FIG. 5. The annular wall 94 includes an outer portion 100 and an inner portion 102, as shown in FIG. 4, with the outer portion 100 positioned concentrically disposed about the inner portion 102. Traveling around the circumference of the upper portion 64, it is seen that the outer portion 100 includes alternating flats 104a, 104b and raised walls 106a, 106b. The inner portion 102 has a similar alternating configuration of flats 108a, 108b and walls 110a, 110b. Another aspect of the upper portion 64 are gap spacings 112a, 112b, 112c, 112d that separate walls of the outer portion 100 and inner portion 102 around the circumference of the annular wall 94. When the upper portion 64 is coupled to the lower portion 66, the gap spacings 112 may be aligned with similar gap spacings 113a, 113b, 113c, and 113d in the lower portion 66 to form openings through which the cable 18 may extend, such as openings 60, 62 shown in FIG. 2.

With reference to FIG. 4, connecting the upper portion 64 to the lower portion 66 involves positioning a wall 116a of the lower portion 66 onto flat 104a of the outer portion 100. Similarly, an outer wall 116b will be positioned on flat 104b and inner walls 118a, 118b are positioned on flats 108a, 108b. Walls 106a,b, 110a,b, 116a,b, and 118a,b are configured to provide a friction fit to couple the upper portion 64 and the lower portion 66.

The upper portion 64 and the lower portion 66 may also include structural features to guide the cable 18 as it is removed from the cable holder 12. For example, adjacent the gap spacing 112b is a chamfered shoulder 134 that connects the annular wall 94 and the side wall 98a. The lower portion 66 may also have one or more chamfered shoulders 135, as shown in FIG. 5. The chamfered shoulder 135 may guide the cable 18 along an axis that extends tangentially to the circumference of the cable coiled within the cable holder 12 (see FIGS. 6 and 7).

By one approach, the lower portion 66 (and the upper portion 64) may have a coupling portion 124b positioned within the center of the lower wall 96b. In one instance, the lower wall 96b, the upstanding side wall 98b, and the coupling portion 124 may form a circular guide track 177. The coupling portion 124b includes an upstanding wall 126b that extends between the lower wall 96b and a flat coupling wall 128b. The flat coupling wall 128b of the lower portion 66 may abut a flat coupling wall 128a of the upper portion 64 when the two portions 64, 66 are coupled together. Although the coupling walls 128a, 128b are shown as having a generally flat configuration, other configurations of the coupling walls may be used, if desired, which provide close abutment of the coupling walls when the upper portion 64 and lower portion 66 are coupled together.

The coupling portions 124a, 124b may also include a mating recess 130a, 130b and a mating projecting member 132a, 132b, respectively. The mating recess is sized to removably receive the mating projecting member therein. The interaction between the mating projecting member 132a and the mating recess 130b as well as the interaction between the mating recess 130a and mating projecting member 132b provides two press-fit connections that provide a frictional fit between the coupling portions 124a, 124b to hold the upper and lower portions 64, 66 together. By another approach, each of the upper and lower portions 64, 66 may include either a mating recess 130 or a mating projecting member 132 instead of one of each as shown in FIG. 4. By yet another approach, the upper and lower portions 64, 66 may be held together at the coupling portions 124a, 124b via a weld, glue, fastener, or other mechanical or chemical fastening mechanism as known in the art.

Figure 6:
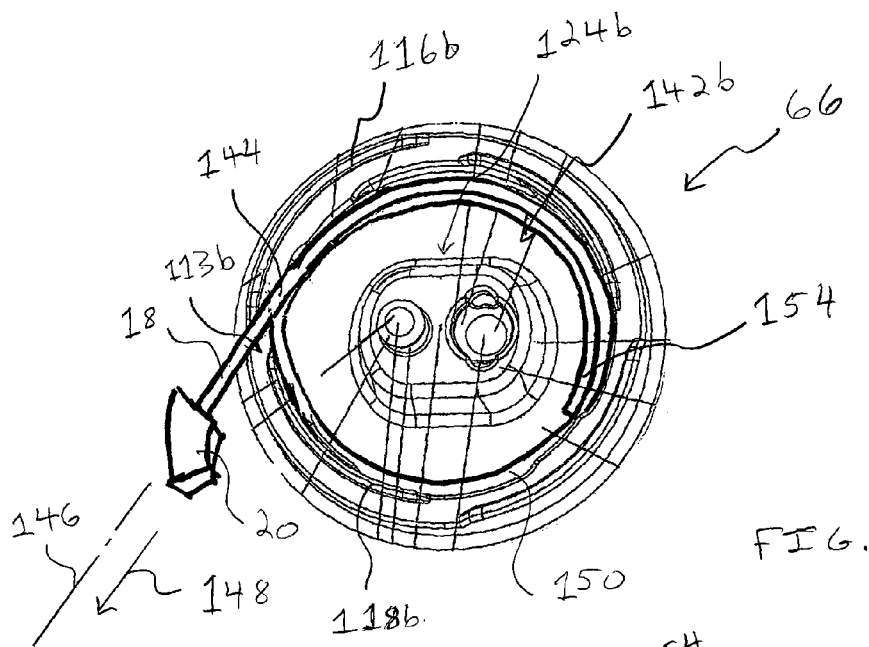
FIGS. 6 and 7 are perspective views of the upper portion of the cable holder of FIG. 4 depicting the cable being pulled in a tangential direction out from a circular guide track in the cable holder lower portion.
Figure 7:
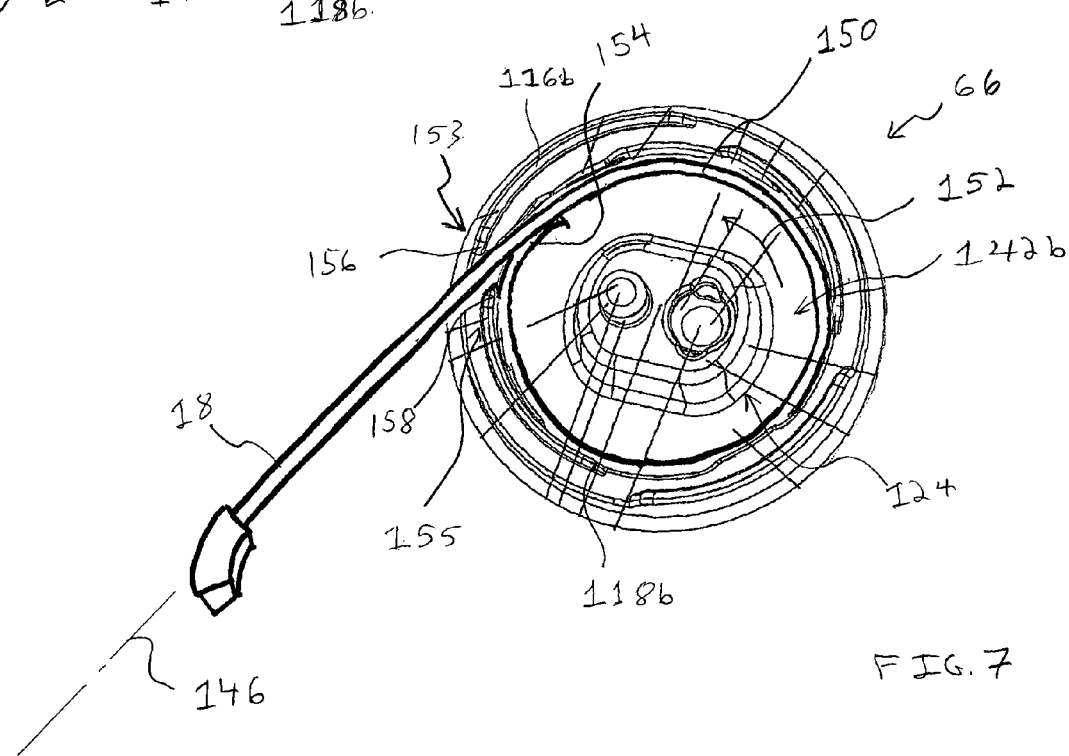

Turning to FIG. 5, the cable holder 12 is assembled by bringing the upper portion 64 together with the lower portion 66 such that the mating projecting member 132b engages with mating recess 130a and mating recess 130b engages with the mating projecting member 132a. With reference to FIGS. 5-7, when the upper and lower portions 64, 66 are coupled together, the cooperating structures 74a, 74b define an interior space within the cable holder 12 comprising interior spaces 142a, 142b of the upper and lower portions 64, 66.

In FIGS. 6 and 7, the upper portion 64 is not depicted so that the cable 18 can be shown in the lower portion 66, which forms the circular guide track 177. An elongated portion 144 of the cable 18 extends through the gap spacing 113b such that the connector 20 is positioned outside of the lower portion 66.

Although FIGS. 6 and 7 do not show upper portion 64 for ease of illustration, the cable 18 is generally removed from the cable holder 12 having the configuration of FIG. 2 with the upper and lower portions 64, 66 coupled together. The cable 18 may be removed from the interior space 142b by grasping the connector 20 and pulling the cable 18 along an axis 146 generally in direction 148. Drawing the cable 18 along the axis 146 causes the cable 18 to uncoil from its coiled configuration 150 within the interior space 142b and to rotate in direction 152, as shown in FIG. 7.

The presence of the coupling portion 124b generally restricts movement of the cable 18 within the interior space 142b except for circumferential movement around the coupling portion 124b. Such restriction of movement prevents kinking and damage to the cable 18. The wall 116b includes a guide structure 153 at one end of the gap spacing 113b and the wall 118b includes a guide structure 155 at the other end of the gap spacing 113b. More particularly, the guide structures 153, 155 may comprise a pair of opposed inclined portions 156, 158 that extend upward and generally increase in height heading away from the gap spacing 113b. The opposed inclined portions 156, 158 generally define a U-shape that, in combination with corresponding structures of the upper portion 66, define opening 62, as shown in FIG. 2. A pair of opposed inclined portions 157, 159 similar to the portions 156, 158 are shown in FIG. 5.

Returning to FIG. 1, the cable holder 12 is installed in direction 22 onto floor 26 of a recessed region 24 of the inner tray 14. In one aspect, cable holder 12 may have a generally annular configuration and the inner tray 14 may have a complimentary curved side wall 28 that is similar or identical to the curvature of the cable holder 12 and fixes the cable holder 12 against a pair of generally straight sidewalls 30, 32 within the inner tray 14. The inner tray 14 may have a flange 34 extending about the periphery thereof with a sealing area 36 configured to receive a peelable film (not shown) to seal the cable holder 12 in the inner tray 14. Generally, the peelable film advantageously permits the cable holder 12 to remain sterile, even if inner tray 14 is not provided in the optional outer tray 16.

By one approach, once the cable holder 12 is positioned within the inner tray 14, the inner tray 14 can be inserted in direction 38 into a recessed region 40 of the outer tray 16. In particular, the floor 26 of the inner tray 14 may rest against a floor 42 of the outer tray 16. In one aspect, the outer tray 16 has a sidewall 44 with a curvature configured to permit the curved sidewall 28 of the inner tray 14 to be held by the complementary sidewall 44 of the outer tray 16.

In another aspect, the outer tray 16 has an inner flange 46 sized slightly wider than the flange 34 of the inner tray 14 such that the flange 34 may nest on the inner flange 46 when the inner tray 14 is inserted in the recessed region 40 of the outer tray 16. The outer tray 16 also includes a pair of recessed corners 48, 50. The inner tray 14 may include a gripping portion 52 that is separated by a gap spacing from curved wall 54 of the recessed corner 48 when the inner tray 14 is positioned within the recessed region 40. The spacing between the curved wall 54 and the gripping portion 52 permits a user to readily insert a finger beneath the gripping portion 52 and pull the inner tray 14 upward out of the recessed region 40 of the outer tray 16.

The outer tray 16 also has an outer flange 56 with a sealing area 58 similar to the sealing area 36 of the inner tray 14. More specifically, with the inner tray 14 and cable holder 12 disposed within the recessed region 40, a peelable sheet (not shown) may be adhered to the sealing area 58 to enclose the cable holder 12 and the inner tray 14 within the outer tray 16. Further, the sealed inner tray 14 with the cable holder 12 may be sterilized after being inserted into the recessed region 40 of the outer tray 16. By sealing the sterilized cable holder 12 and the inner tray 14 within the outer tray 16 prior to sterilization, an operating room technician may easily peel the film from the sealing area 58 of the outer tray 16 and deposit the sterile inner tray 14 with the cable holder 12 into a sterile surgical environment.

Figure 8:
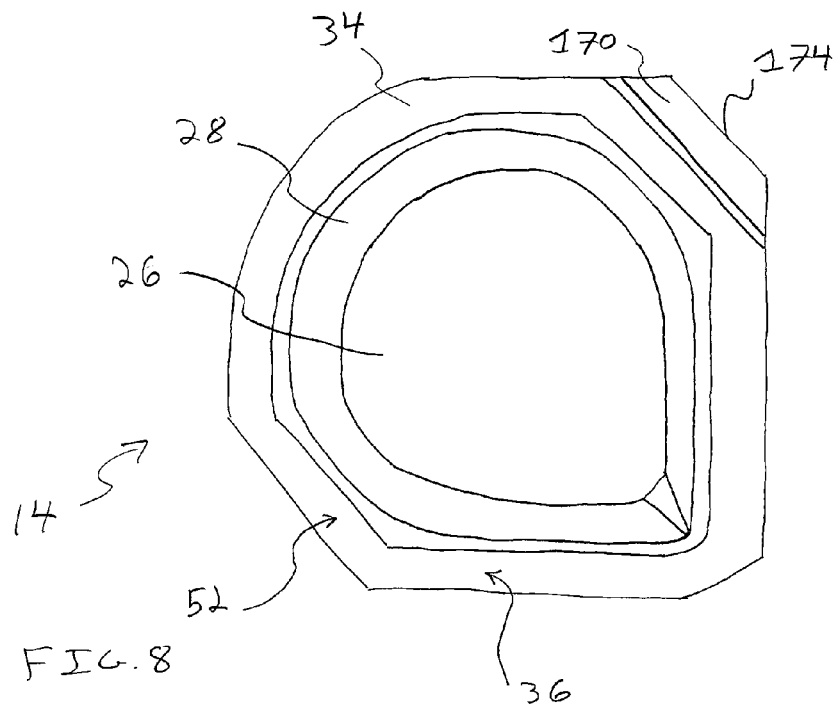
FIG. 8 is a plan view of the inner tray of FIG. 1 showing a flange of the inner tray that engages the outer tray.
Figure 9:
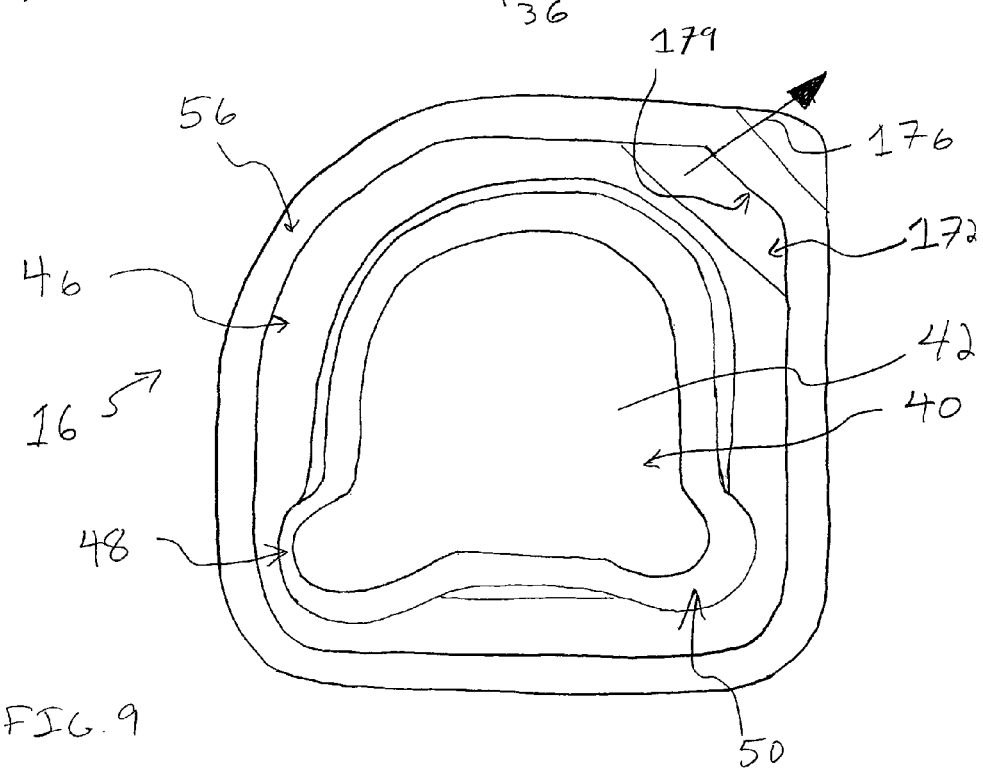
FIG. 9 is a plan view of the outer tray of FIG. 1 showing a recessed region for receiving the inner tray.

With reference to FIGS. 8 and 9, the inner tray 14 has a flange 34 that comprises both the gripping portion 52 and an angled flange portion 170. The angled flange portion 170 may be disposed slightly lower than the surrounding portions of the flange 34 such that the peelable film adhered to the sealing area 36 of the inner tray 14 may be spaced initially from the angled flange portion 170. This initial spacing may permit the user to readily separate the peelable film from the inner tray 14. Further, the angled flange portion 170 may rest within a seat 172 formed in the inner flange 46 of the outer tray 16, as shown in FIG. 9. More specifically, the seat 172 may be lower than the outer flange 56 and the inner flange 46. The angled flange portion 170 resting within the seat 172 acts as a pivot point for the inner tray 14 when the gripping portion 52 is used to pull the inner tray 14 upwardly from the recessed region 40 of the outer tray 16. The seat 172 may include a wall portion 179 extending downward from the outer flange 56 such that an edge 174 of the inner tray 14 abuts the wall portion 179. In this manner, the inner tray 14 may be restricted from sliding in a direction 176 along the outer tray 16 to improve the ease of use of the package 10.

Figure 10:
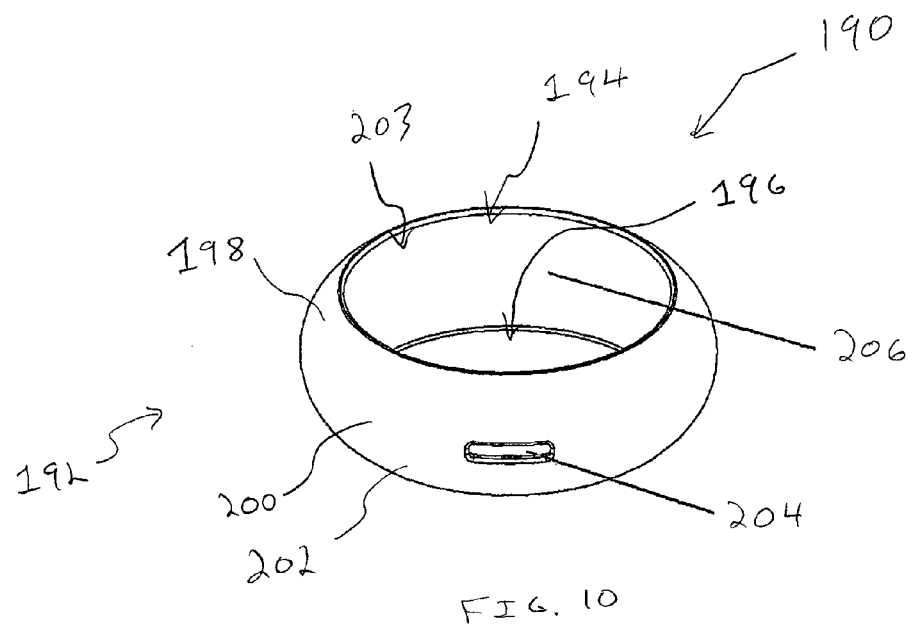
FIG. 10 is a perspective view of an alternative cable holder having an annular side wall with an opening formed therein.

In another aspect, the cable holder can be provided as shown in FIG. 10. The cable holder 190 has a body 192 with an upper opening 194 and a lower opening 196. The body 192 includes an upper wall portion 198, a side wall portion 200, and a lower wall portion 202. The cable holder 190 defines an interior space 203 configured to receive a coiled cable (not shown). By one optional approach, the cable holder 190 may include an opening 204 in at least one of the wall portions, shown in FIG. 10 as an opening in the side wall portion 200, through which an end of the coiled cable can extend. In one aspect, the side wall portion 200 has a generally annular shape and extends radially farther than the upper and lower wall portions 198, 202. The body 192 may include a curved interior surface 206 such that the interior surface of the side wall portion 200 has a generally annular shape that extends radially farther than interior surfaces of the upper and lower wall portions 198, 202. In this form, the upper and lower wall portions 198, 202 cooperate to confine the cable within the interior space 203 of the cable holder 190. Such a curved interior surface is effective to contain the coiled cable 18 within the interior space 203 of the cable holder 190.

Figure 11:
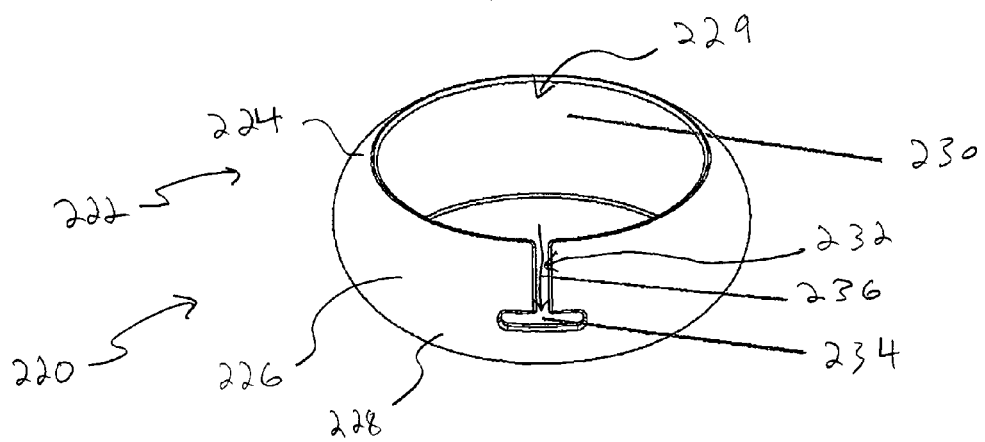
FIG. 11 is a perspective view of an alternative cable holder having an annular side wall with a T-shaped opening formed therein.

In yet another aspect, the cable holder can be provided as shown in FIG. 11. A cable holder 220 has a body 222 with an upper wall portion 224, a side wall portion 226, and a lower wall portion 228. The body 222 defines an interior space 229 for receiving the cable 18 in a coiled configuration. Like the cable holder 190, the cable holder 220 may include a curved interior surface 230 configured to contain the coiled cable. By one approach, the cable holder 220 may also include a slot 232 formed in the upper wall portion 224 that extends downwardly to an opening 234 which is configured perpendicularly to the slot. The slot 232 permits a connector end of the cable 18 to be slidably received in a direction 236 along the slot 232 and into the opening 234.

Figure 12:
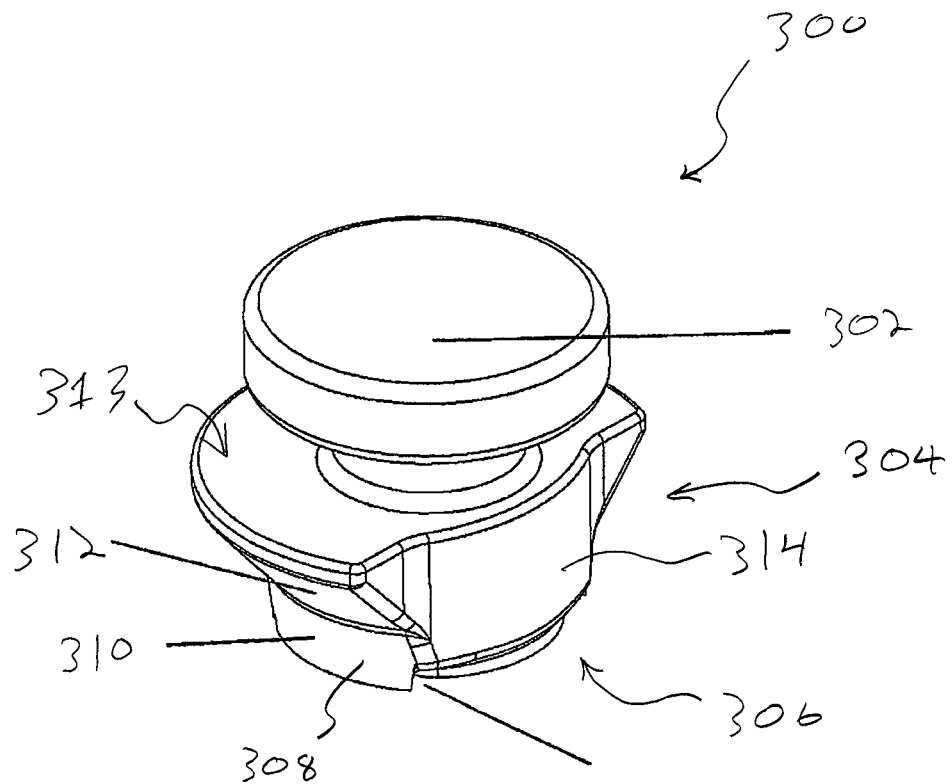
FIG. 12 is a perspective view of a fixture having a handle and a body extending therefrom that may be used to install a surgical cable into the lower portion of the cable holder of FIG. 4.
Figure 13:
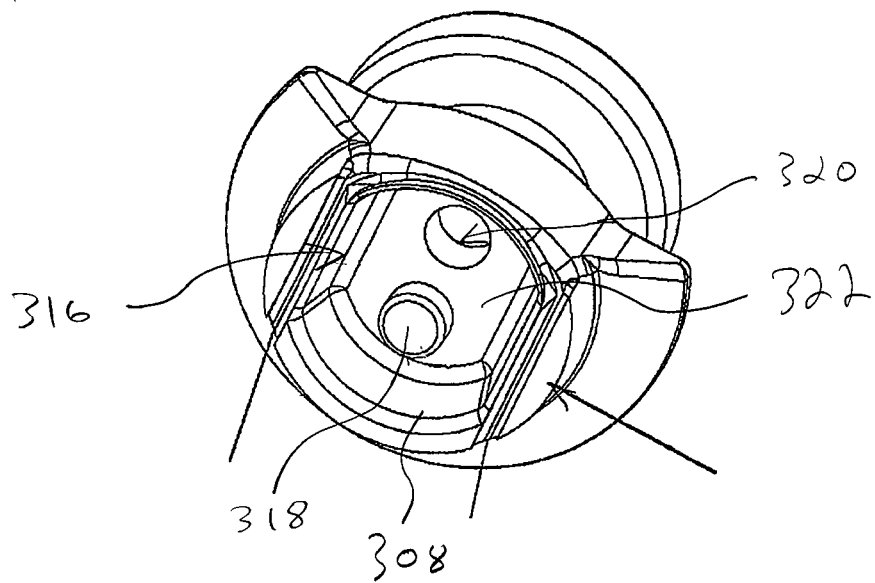
FIG. 13 is a perspective view of the fixture of FIG. 12 showing a coupling portion of the fixture configured to engage a corresponding structure on the lower portion of the cable holder of FIG. 4.

Turning to FIGS. 12-18, a tool and method for installing a surgical cable within a package is shown. As shown in FIG. 12, a tool or fixture 300 is provided which comprises a handle 302, an elongate body 304 extending from the handle 302, and a coupling portion 306 opposite the handle 302. The coupling portion 306 is configured to engage a coupling portion in a cable holder, such as coupling portion 124b in lower portion 66 or coupling portion 124a in upper portion 64.

The coupling portion 306 includes an opening 316 configured to receive, for example, the coupling portion 124b of the lower portion 66. The coupling portion 306 further includes a projecting member 318 configured to extend into and engage the mating recess 130b of the lower portion 66 to provide a press-fit engagement. The coupling portion 306 also includes a mating recess 320 configured to engage projecting member 132b of lower portion 66. When the projecting member 318 and the mating recess 320 of the coupling portion are press-fit together, with the mating recess 130b and mating projection member 132b of the lower portion 66, the fixture is releasably coupled to the lower portion 66.

Figure 14:
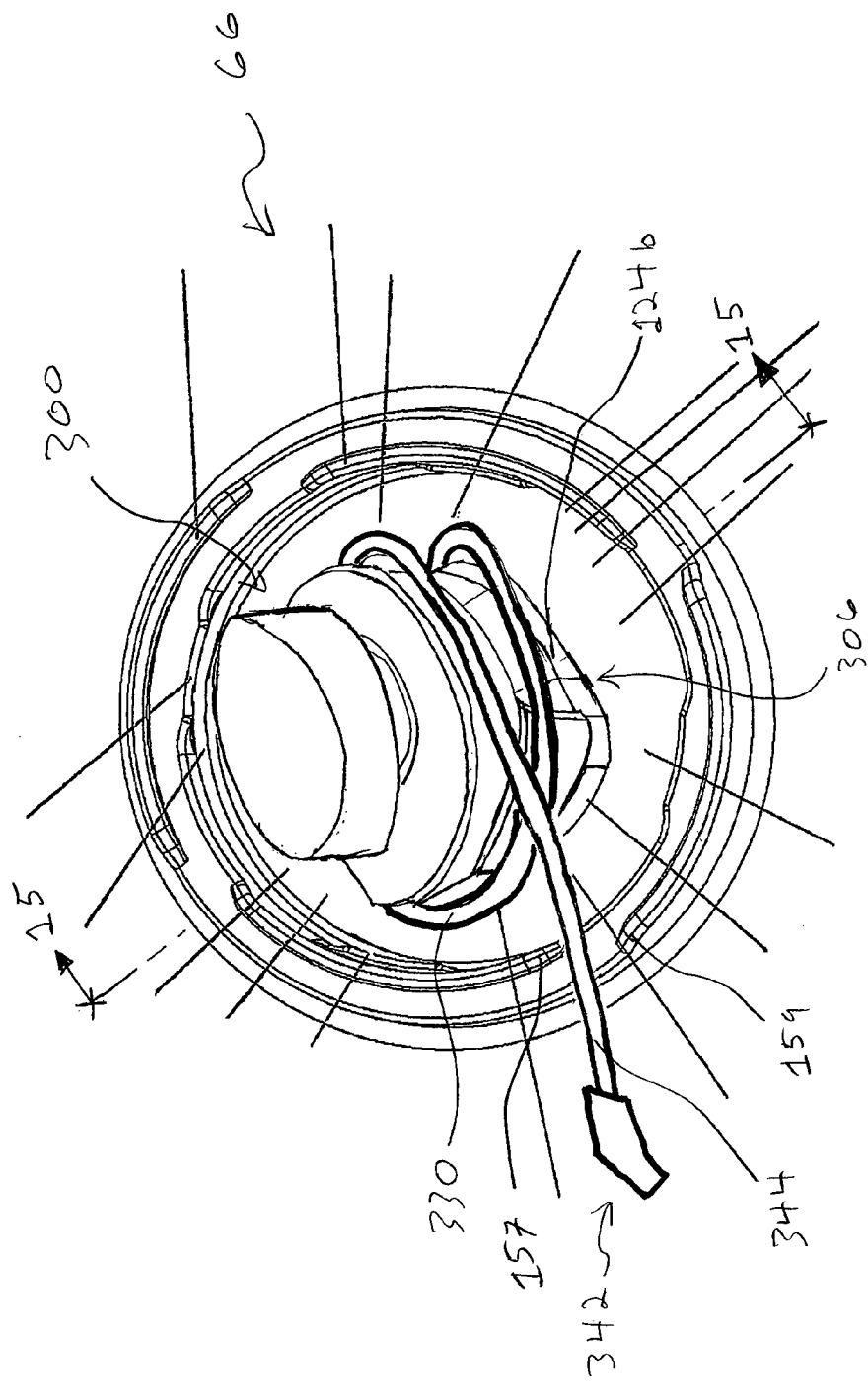
FIG. 14 is a perspective view of the fixture of FIG. 12 connected to the lower portion of the cable holder of FIG. 4.

Further, when the coupling portion 306 is coupled to the coupling portion 124b of the lower portion 66, for example, a skirt 308 of the fixture 300 extends downwardly and is configured to provide a frictional fit between the skirt 308 and upstanding wall 126b of lower portion 66 to further couple the fixture 300 to the lower portion 66. As shown in FIG. 14, the fixture 300 engages the coupling portion 124b of the lower portion 66 and permits a surgical cable 330 to be wound around the fixture 300. Although not pictured herein, the coupling portion 306 may be similarly coupled to upper portion 64.

The fixture 300 also includes a cylindrical surface 310 and a tapered surface 312 which the cable 18 may be wound about. Further, the fixture 300 may include a shoulder portion 313 and an alignment portion 314 to improve a user's grip on the fixture 300.

Figure 15:
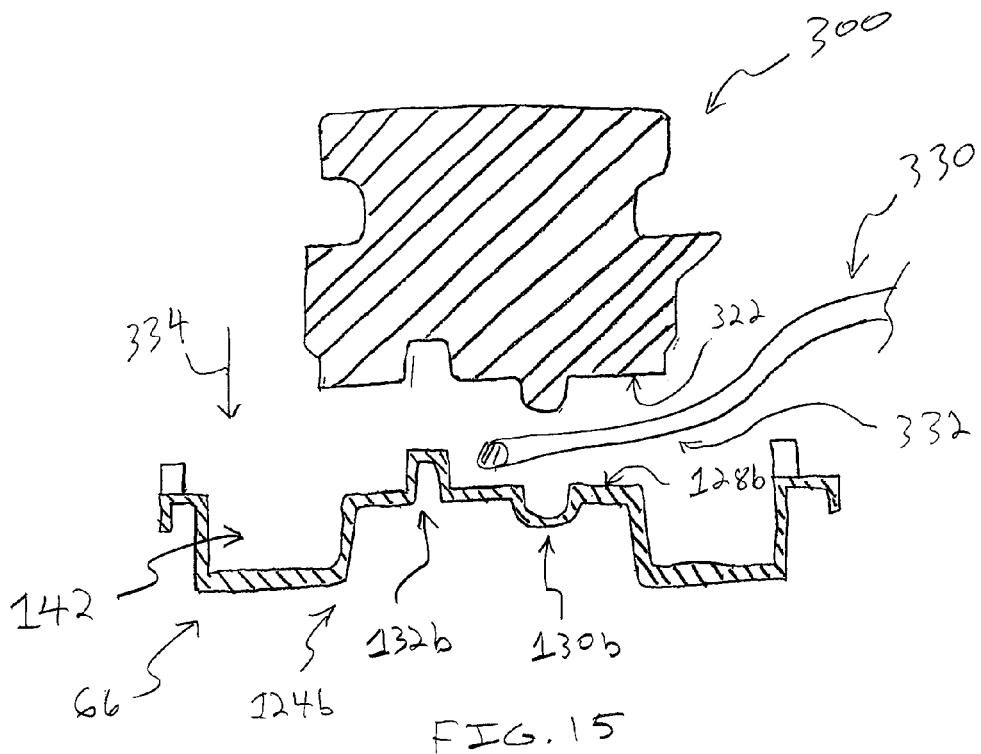
FIGS. 15-18 are a series of cross-sectional views taken across the line 15-15 in FIG. 14 showing one approach of installing a surgical cable into the interior space of the lower portion of the cable holder.
Figure 16:
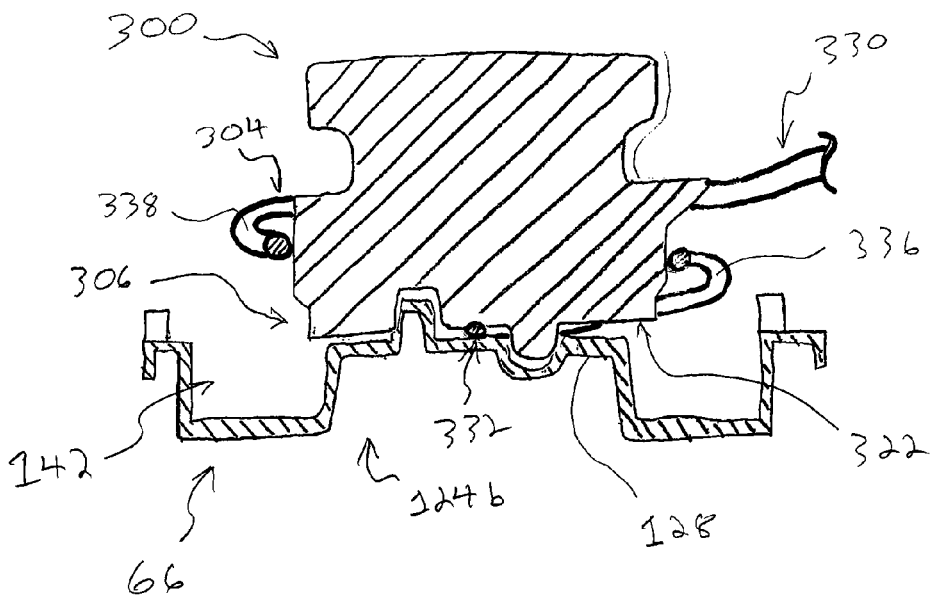

FIGS. 15-18 illustrate a method of inserting the surgical cable 330 into the lower portion 66, as taken across line 15-15 in FIG. 14. Initially, a free end 332 of the cable 330 may be placed between the flat coupling wall 322 of the fixture 300 and the flat coupling wall 128b of the lower portion 66 before shifting the fixture downward in direction 334 to trap the free end 332 therebetween, as shown in FIG. 16. By another approach, the free end 332 of cable 330 may remain unrestrained during installation of the cable 330 into the lower portion 66.

With the fixture 300 coupled to the coupling portion 124b of lower portion 66, as shown in FIGS. 15 and 16, the cable 330 can then be wrapped upwardly away from the coupling portion 306 of the fixture 300 in a helical manner around the elongate body 304. The coiled cable is disposed about the fixture 300, as illustrated by coil portions 336, 338 in FIG. 16.

Figure 17:
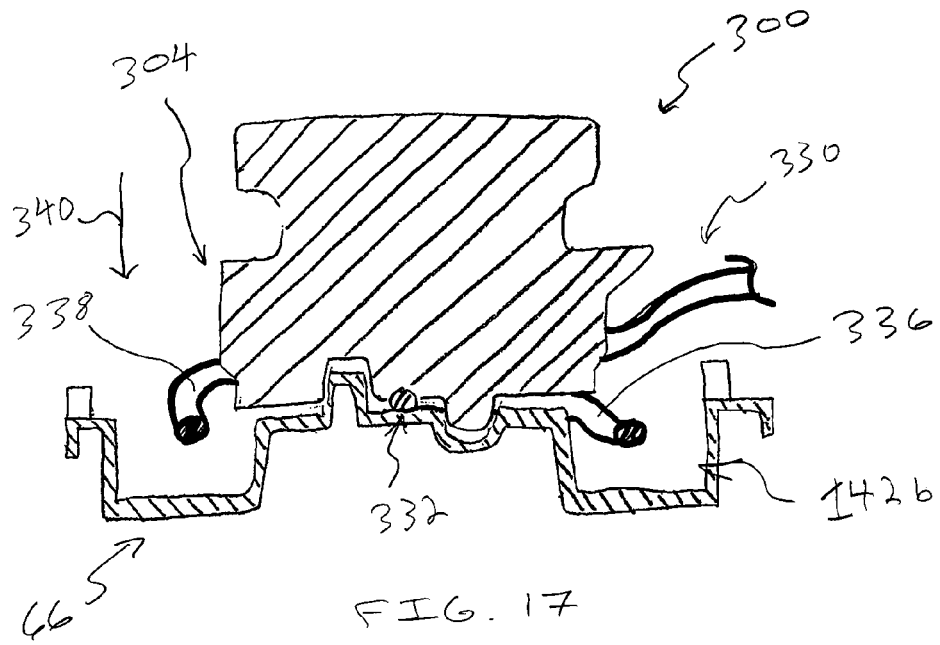

The coiled cable 330 can then be slid or displaced from the elongate body 304 in direction 340 into the interior space 142b of the lower portion 66, as shown in FIG. 17. This positions the coil portions 336, 338 within the interior space 142b of the lower portion 66. In one approach, the helical configuration of the cable 330 is generally maintained as the cable is displaced into the lower portion 66. This permits the cable 330 to be inserted into the lower portion 66 in a tightly coiled configuration.

Figure 18:
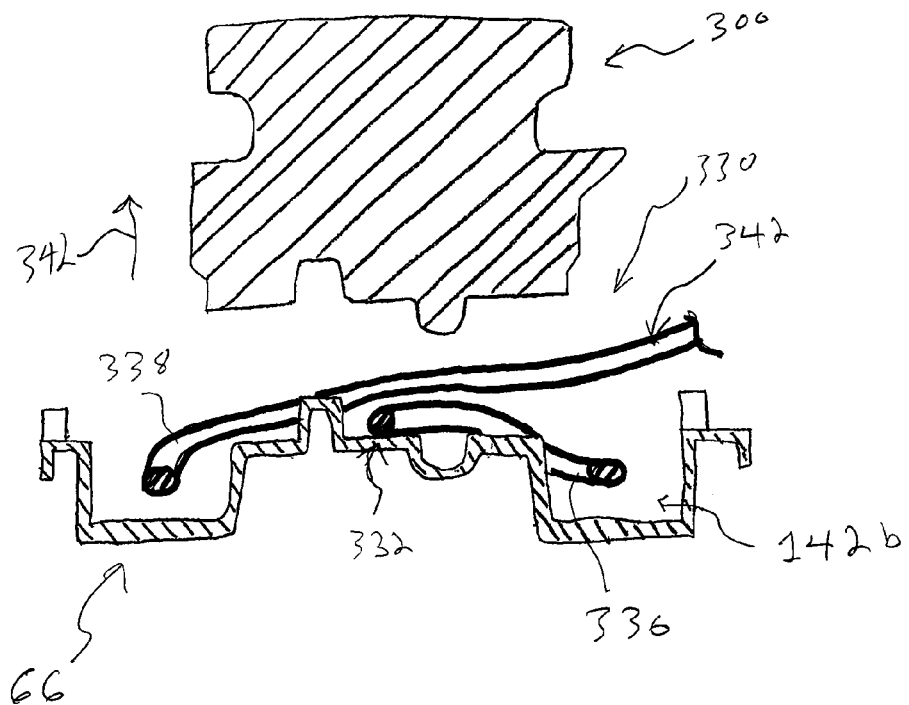

As shown in FIG. 18, the fixture 300 can then be removed from the coupling portion 124b in direction 342 upwardly from the lower portion 66. If the free end 332 of cable 330 was held between the fixture 300 and the coupling portion 124b of the lower portion 66, the free end 332 may be moved into the interior space 142b with the coil portions 336, 338.

A connector end 342 of the cable 330 may be positioned outside of the lower portion 66 before the upper portion 64 is connected to the lower portion 66. With reference to FIG. 14, an elongate portion 344 of the cable 330 may be laid through the U-shaped opening between the pair of opposed inclined portions 157, 159. When the upper portion 64 is connected to the lower portion 66, the inclined portions 157, 159 combine with a pair of opposed inclined portions of the upper portion 64 to form opening 62, as shown in FIG. 2. This procedure produces the cable holder 12 with the coiled cable 330 positioned therein and a connector end 342 of the cable 330 positioned outside of the cable holder 12.

The cable holders 12, 190, and 220, as well as inner tray 14 and outer tray 16, may be made from a variety of materials.

For example, the cable holder may be made from polyester laminates, polycarbonate, or other thermoformable sheet plastics. By one approach, the cable holder may be made from polyethylene terephthalate glycol. The various components of the package 10 may be sterilized using gamma rays or ethylene oxide gas.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A method of packaging a surgical cable, the method comprising:
    providing a fixture and a cable holder that are separate and distinct from each other, wherein the cable holder has an upper portion and a lower portion;
    positioning the separate and distinct fixture adjacent the lower portion of the cable holder;
    aligning the fixture with the lower portion of the cable holder;
    wrapping the cable around an elongate body portion of the fixture;
    sliding the wrapped cable off of the body portion of the fixture and into the lower portion of the cable holder that is separate and distinct from the fixture;
    positioning a connector end of the cable outside of the lower portion of the cable holder;
    moving the fixture away from the lower portion of the cable holder; and
    connecting the upper portion of the cable holder to the lower portion of the cable holder after moving the fixture away from the lower portion to retain the cable within an interior space formed by the upper and lower portions, the connector end of the cable extending through an opening of the cable holder to an exterior thereof which allows the cable to be removed from the interior space.

2. The method of claim 1 further comprising locating a free end of the cable between the fixture and the lower portion of the cable holder while wrapping the cable around the body portion of the fixture.

3. The method of claim 2 further comprising coupling the fixture to the lower portion of the cable holder to trap the free end of the cable between the fixture and the lower portion of the cable holder.

4. The method of claim 1 further comprising wrapping the cable around the elongate body portion of the fixture in a generally helical configuration and maintaining the helical configuration of the cable while sliding the cable off of the body portion of the fixture to position the cable within the lower portion of the cable holder in a coiled configuration.

5. The method of claim 1 wherein the upper portion of the cable holder is disconnected from the lower portion of the cable holder while wrapping the cable around the body portion of the fixture and sliding the wrapped cable off of the body portion of the fixture and into the lower portion of the cable holder.

6. The method of claim 1 further comprising locating a free end of the cable in the lower portion of the cable holder while wrapping the cable around the body portion of the fixture.

* * * * *